United States Patent [19]

Ishihara et al.

[11] Patent Number: 6,066,595

[45] Date of Patent: May 23, 2000

[54] HERBICIDE CONTAINING PHYTOPATHOGENIC MICROORGANISMS

[75] Inventors: Kazuto Ishihara; Seiya Nikumaru; Kenichi Yamaguchi; Takeshi Nakamura, all of Chiba, Japan

[73] Assignee: Mitsui Chemicals, Inc., Japan

[21] Appl. No.: 08/961,219

[22] Filed: Oct. 30, 1997

[30] Foreign Application Priority Data

Nov. 5, 1996 [JP] Japan ........................................ 292461

[51] Int. Cl.[7] ............................ A01N 25/08; A01N 63/00
[52] U.S. Cl. ................................................................. 504/117
[58] Field of Search ............................................. 504/117

[56] References Cited

U.S. PATENT DOCUMENTS

| 5,424,271 | 6/1995 | Yamaguchi et al. | 504/117 |
| 5,434,121 | 7/1995 | Gohbara et al. | 504/117 |

FOREIGN PATENT DOCUMENTS

| 605221 | 7/1994 | European Pat. Off. . |
| 06321721 | 11/1994 | Japan . |
| 08040816 | 2/1996 | Japan . |

OTHER PUBLICATIONS

Database WPI, Section Ch, Week 9544, Derwent Publications Ltd., London, GB; Class C05, AN 95–340151, XP002055603 & JP07233020A (Japan Tobacco Inc.), Sep. 5, 1995 *abstract*.

Database WPI, Section Ch, Week 9629, Derwent Publications Ltd., London, GB; Class A97, AN 96–283371, XP002055604 & JP08119816A (Japan Tobacco Inc.), May 114, 1996 *abstract*.

Database WPI, Section Ch, Week 9629, Derwent Publications Ltd., London, GB; Class C05, AN 96–283372, XP08119817A & JP08119817A (Japan Tobacco Inc.), May 14, 1996 *abstract*.

W.J. Connick, "Formulation of Living Biological Control Agents with Alginate ACS Symposium Series 371", 1988, Washington, DC, US, pp. 240–250, XP002055601.

Database WPI, Section Ch, Week 9215, Derwent Publications Ltd., London, GB; Class C03, AN 92–120843, XP002055606 & JP04066509A (Nissan Chem. Ind. Ltd.), Mar. 2, 1992 *abstract*.

Biological Abstracts, vol. 87, Philadelphia, PA, US; Abstract No. 68395, H.Z. Yang et al, Quantitative Structure–Activity Study of Herbicidal O–Aryl–O–Ethyl–N–Isopropylphosphoramidothioates, XP002055602 *abstract* & Pestic. Biochem. Physiol., vol. 26, No. 3, 1986, pp. 275–283.

*Primary Examiner*—S. Mark Clardy
*Attorney, Agent, or Firm*—Burns, Doane, Swecker, & Mathis, L.L.P.

[57] ABSTRACT

A herbicide containing phytopathogenic microorganisms for surface application on water was obtained by a method in which the phytopathogenic microorganisms, which have virtually no adhered surfactant and are pathogenic against non-useful plants having a hydrophobic surface, are adhered to or combined with a submersible base.

21 Claims, No Drawings

HERBICIDE CONTAINING PHYTOPATHOGENIC MICROORGANISMS

BACKGROUND OF THE INVENTION

1. Field of the Invention

The present invention relates to a herbicide containing phytopathogenic microorganisms for surface application on water comprising phytopathogenic microorganisms which are pathogenic against non-useful plants having a hydrophobic surface, and are themselves hydrophobic on the surface but with virtually no adhered surfactant, and a submersible base, and a process for producing the same.

2. Description of the Related Art

Environmental pollution caused by excessive use of synthetic organic agricultural chemicals or reduced herbicidal effectiveness due to the appearance of pathogenic insects or weeds which have developed chemical resistance has become a serious social problem. The effects of synthetic organic agricultural chemicals on humans or the natural environment have become a media issue. Biological agricultural agents have attracted attention as a solution to these problems, and research and development in this field has been facilitated.

Research and development into herbicides containing phytopathogenic microorganisms has been active primarily in the United States. Today, DeVine (a product of Abbott Laboratories) using chlamydospores of *Phytophthora palmivola*, a phytopathogenic microorganism effective against strangle vein (*Morrenia odorate*), an Asclepiadaceae weed, Collego (a product of Ecogen) using spores of *Colletotrichum gloeosporioides*, a phytopathogenic microorganism effective against northern jointvetch (*Aeschynomene viginica*), a leguminous weed, and others are commercially available.

Other ongoing research with phytopathogenic microorganisms includes those of genus Hypomycetes having pathogenicity to kuroguwai (*Eleocharis kuroguwaiohwi*), a rice paddy weed, and *Cercospora rodmanii* having pathogenicity against water hyacinth (*Eichhornia crassipes*), an aquatic plant.

Meanwhile, the development of herbicides containing phytopathogenic microorganisms against barnyard weeds is progressing in Japan, and such herbicides and methods of application have been proposed (Japanese Patent Laid-open (Kokai) No. 1994/321721; Japanese Patent Laid-open (Kokai) No.1996/40816). Japanese Patent Laid-open (Kokai) No. 1994/321721 discloses a technique in which a new microorganism belonging to genus Curvularia was suspended in an organic solvent supplemented with a surfactant to better preserve said microorganisms and to improve their dispersion in water.

In such herbicides containing phytopathogenic microorganisms, it is advantageous to use a conidium of a phytopathogenic microorganism because of its durability. However, a conidium having a hydrophobic surface has been difficult to produce and use as a herbicide because of its inherent low affinity to water.

For example, conidia of *Drechslera monoceras*, which is pathogenic against barnyard grass, a weed in rice paddies, have a higher specific gravity than water, but when directly seeded on rice paddies, the conidia float on the surface of the rice paddies. If the conidia float on the water surface and cannot submerse, the conidium has a decreased chance to make contact with the barnyard grass. Thus, the use of this microorganism cannot have a sufficient herbicidal effect against barnyard grass. Conidia float on the surface of rice paddies because the surface of the conidia is inherently hydrophobic such that they repel water due to the surface tension of water. Conventionally, in order to solve this problem, a surfactant or the like is added to a conidium fraction so as to increase the affinity of the conidia to water (Japanese Patent Laid-open No. 1994/321721).

The hydrophobic surface of a conidium of phytopathogenic microorganisms also has an adverse effect on the production of a conidium fraction, specifically, the aggregation of the conidia causes difficulty in handling and lowers recovery. A surfactant has conventionally been used to resolve this problem.

Thus in the production of phytopathogenic microorganisms having a hydrophobic surface, and the formulation of a herbicide containing said microorganisms as an effective component, said microorganisms have always had a sufficient amount of adhered surfactant.

SUMMARY OF THE INVENTION

The present invention is intended to improve the effectiveness of herbicides containing phytopathogenic microorganisms for surface application on water, namely, to improve the herbicidal activity per unit number of microorganisms.

An objective of the present invention is to provide a herbicide containing phytopathogenic microorganisms for surface application on water, in which said microorganisms can submerse while retaining their natural surface hydrophobicity.

Generally, the first step in the infection of weeds by phytopathogenic microorganisms is the contact and adhesion of said microorganisms onto the surface of the leaves. The present inventors understand the phenomena occurring on the surface of the leaves to be as follows: When phytopathogenic microorganisms infect weeds whose leaves are naturally hydrophobic on the surface, the hydrophobic interaction strengthens the adhesiveness of said microorganisms to the weeds. Conventional mycoherbicides are always supplemented with surfactants so that the surface of the microorganisms acquires apparent hydrophilicity. As a result, although the phytopathogenic microorganisms can easily submerse and disperse in water to facilitate contact between said microorganism and weeds, the hydrophobic interaction of said microorganisms is adversely weakened such that those microorganisms which reach the leaf surfaces cannot adhere sufficiently, resulting in insufficient herbicidal effectiveness.

In view of these circumstances, the present inventors formulated a preparation which can submerse the phytopathogenic microorganisms while retaining their natural surface hydrophobicity, and studied its herbicidal effect on plants. Surprisingly, it was found that this preparation has a markedly better herbicidal effect than those containing phytopathogenic microorganisms having surfactants adhered on the surface. The present inventors have completed the present invention based on this finding.

The present invention provides the followings:

1. A herbicide containing phytopathogenic microorganisms for surface application on water comprising phytopathogenic microorganisms which are pathogenic against non-useful plants having a hydrophobic surface, and are themselves hydrophobic on the surface but with virtually no adhered surfactant, and a submersible base.

2. A method of producing a herbicide containing phytopathogenic microorganisms for surface application on water, wherein phytopathogenic microorganisms which are pathogenic against non-useful plants having a hydrophobic surface, and are themselves hydrophobic on the surface, are produced, and said phytopathogenic microorganisms are adhered to or combined with a submersible base, while retaining the surface hydrophobicity of the phytopathogenic microorganisms.

3. A method of producing a herbicide containing phytopathogenic microorganisms for surface application on water, wherein phytopathogenic microorganisms, which are pathogenic against non-useful plants having a hydrophobic surface, and are themselves hydrophobic on the surface, are produced, and said phytopathogenic microorganisms are dispersed among particles of a submersible base, while retaining the surface hydrophobicity of the phytopathogenic microorganisms.

The present invention provides a novel herbicide containing phytopathogenic microorganisms for surface application on water, in which phytopathogenic microorganisms retain their surface hydrophobicity but acquire submersibility. The herbicide containing phytopathogenic microorganisms for surface application on water according to the present invention remarkably improves the weed controlling effect as compared with conventional herbicides containing phytopathogenic microorganisms because adhesiveness to plants to be controlled is facilitated by hydrophobic interaction between the retained hydrophobicity on the surface of the phytopathogenic microorganisms and the plant surface. Thus, the herbicide containing phytopathogenic microorganisms for surface application on water requires smaller numbers of microorganisms than conventional herbicide containing said microorganisms to attain the same level of weed controlling effect, thus reducing the cost of the herbicide.

DETAILED DESCRIPTION OF THE INVENTION AND PREFERRED EMBODIMENTS

Phytopathogenic microorganisms used in the present invention are those which are pathogenic against plants having a hydrophobic surface. The microorganisms, however, are not pathogenic against useful crops. Furthermore, the surface of the microorganisms is hydrophobic and a hydrophobic interaction, along with the hydrophobicity of the surface of the plants to be controlled, is necessary for infection by the microorganisms. The following strains are practical examples of microorganisms used in the present invention. However, any other microorganisms which satisfy the abovementioned conditions can also be used.

Examples of phytopathogenic microorganisms used in the present invention are those belonging to genus Drechslera. In particular, *Drechslera monoceras, Drechslera ravenelii* and *Drechslera poae* are suitable. Examples of suitable strains include *Drechslera monoceras* MH-0015 (FERM BP-2652), MH-1889 (FERMBP-3410), MH-2653 (FERMBP-2653), MH-2679 (FERMBP-2656), H-4415 (FERM BP-3413), MH-4418 (FERM BP-3414), MH-5011 (FERM BP-3415), MH-5017 (FERM BP-3411), MH-5018 (FERM BP-3412), MH5511 (FERM BP-3417), MH-9011 (FERM BP-3416), MH111010 (FERM BP-3864), MH-121024 (FERM BP-4498), MH121025 (FERM BP-4499), MH-122124 (FERM BP-4500), MH-122754 (FERM BP-4501), MH-122755 (FERM BP-4502), MH-122756 (FERM BP-4503), MH-1901 (FERM BP-6091) and MH-2001 (FERM BP-6092), *Drechslera ravenelii* MH-0042 (FERM BP-2659), MH-0060 (FERM BP-2657) and MH-2883 (FERM BP-3408), and *Drechslera poae* MH-0122 (FERM BP-2655), MH-2781 (FERM BP-3407) and MH-2895 (FERM BP-3409). These strains are deposited with the abovementioned access numbers at the National Institute of Bioscience and Human-Technology Agency of Industrial Science and Technology, Ministry of International Trade and Industry, 1-3 Higashi 1-Chome Tsukuba City, Ibaraki Prefecture, Japan, according to the Budapest Treaty.

Other examples of phytopathogenic microorganisms appropriate for use in the present invention include strains of *Exserohilum monoceras* MAFF-305452, MAFF-510858, MAFF-511283 and MAFF-511296. These strains can be purchased at the National Institute of Agrobiological Resources, Ministry of Agriculture, Forestry and Fisheries, 1-2 Kannondai 2-Chome, Tsukuba City, Ibaraki Prefecture, Japan.

Phytopathogenic microorganisms used in the present invention can be in a form of either a conidium, oidium or hypha as long as they have a hydrophobic surface and can adhere to plants to be controlled and cause infection. Preferably, the conidium form is used because of its high durability.

A method of producing a herbicide containing phytopathogenic microorganisms for surface application on water can be to formulate a preparation which can disperse and submerge the phytopathogenic microorganisms of the present invention, for example in the form of conidium, while retaining their natural surface hydrophobicity.

The abovementioned phytopathogenic microorganisms, for example in the form of conidium, can be produced by culturing the microorganisms using a general microbial culture method (for example, culturing on a potato-dextrose agar medium for about 3 to 20 days).

In the present invention, the expression "phytopathogenic microorganisms with virtually no adhered surfactant" denotes those not being affected by a surfactant, so that the microorganisms (for example in the conidium form) float on the surface of water due to the surface tension when they are added to an aqueous solution without further treatments.

When a surfactant is used in the process of producing phytopathogenic microorganisms (for example in the conidium form), it has to be thoroughly removed prior to the formulation process. For example, the fraction of phytopathogenic microorganisms is filtrated using an ordinary filter to remove microorganisms with the adhered surfactant and then thoroughly washed.

A submersible base to be used in the present invention is submersible by itself and can adhere to or combine with phytopathogenic microorganisms while retaining their surface hydrophobicity. When the phytopathogenic microorganisms are combined with the base, they can be dispersed and submersed in a solution. Examples of the base according to the present invention include mineral powders such as clay, talc, bentonite, calcium carbonate, diatomaceous earth and white carbon black, and polymers such as polyvinyl alcohol and polyalkylene glycol. However, the base is not limited to these examples as long as it can disperse and submerse the phytopathogenic microorganisms.

A method for producing a formulation which can disperse and submerse phytopathogenic microorganisms comprises mixing phytopathogenic microorganisms with a base while retaining the surface hydrophobicity, then drying and crushing the resulting admixture to adhere to or combine with the base. It does no harm to add additives such as a pasting agent along with the base to the formulation, if appropriate. A pasting agent free from surfactant activity is preferred.

The herbicide thus prepared submerses quickly when applied on the surface of water. The base is then degraded and the conidia are freed in the water.

Furthermore, for better diffusion of the phytopathogenic microorganisms to the surface of water when applied, after the phytopathogenic microorganisms are mixed with the submersible base and are adhered to or combined with the base, a solid surfactant can be added to the resulting material at room temperature. The amount of the surfactant to be added must be determined within a range such that the hydrophobicity of the surface of the phytopathogenic microorganisms in the final preparation can be retained.

In this case, it is preferable that granules of the formulated herbicide are made by crushing and sieving to a diameter of 0.1 to 2 mm, preferably 0.1 to 0.3 mm.

Another method of producing a formulation which can disperse and submerge phytopathogenic microorganisms comprises dispersing the phytopathogenic microorganisms, while retaining their surface hydrophobicity, among base particles. More precisely, base particles previously prepared are mixed with the phytopathogenic microorganisms with virtually no adhered surfactant.

In this case, the base particles have a diameter of 0.1 $\mu$m to 0.1 mm, preferably 1 $\mu$m to 0.01 mm.

Furthermore, in the abovementioned method of dispersing phytopathogenic microorganisms among the base particles in the formulation, in order to improve diffusion of the phytopathogenic microorganisms in water when applied, a surfactant or an additive which gives the herbicide of the present invention surface diffusibility on water can be added to the base before mixing with the phytopathogenic microorganisms. A solid surfactant can be mixed together with the base and the phytopathogenic microorganisms at room temperature as described above. The amount and the type of surfactant and the additive which gives the herbicide of the present invention surface diffusibility on water must be determined within a range such that the hydrophobicity of the surface of the phytopathogenic microorganisms in the final preparation can be retained.

A surfactant in the present invention is an amphipatic substance which can reduce surface tension of naturally phytopathogenic microorganisms when adhered on their surface and turn them apparently hydrophilic. A surfactant in the present invention can be appropriately selected to meet the abovementioned property from the following examples, i.e., nonionic surfactants such as sucrose esters of fatty acid, polyoxyethylenepolyoxypropyleneglycol ether, polyoxyethylenealkyl ether, polyoxyethylenealkylphenyl ether, polyoxyethylene esters of fatty acid and polyoxyethyleneglycol alkyl ether, and anion surfactants such as polyoxyethelenealkylphenyl ether sulfate ammonium salt, polyoxyethylenealkylphenyl ether sulfate sodium salt, sulfonated castor oil and sulfosuccinic acid diallkyl sodium.

The herbicide formulations of the present invention can be any form that is dispersible and submersible in water while retaining the surface hydrophobicity of the phytopathogenic microorganisms to effectively exhibit herbicidal activity. Solid formulations such as powders, granules and powdery granules are preferable. Granules or powdery granules are preferable when the phytopathogenic microorganisms are dispersed and submersed in water by being adhered to or combined with a base while retaining their surface hydrophobicity. Furthermore, granules with a small diameter are preferable because conidia of the phytopathogenic microorganisms each present singly on small granules can be more effective than those present in multiple numbers on large granules. For example, in the case of conidia of *Drechslera monoceras* MH-0015 having a long diameter of about 0.1 mm, an appropriate diameter of granules for the herbicide is 0.1 to 2 mm, preferably 0.1 to 0.3 mm.

When conidia of phytopathogenic microorganisms belonging to genus Drechslera are used in a herbicide of the present invention, the number of conidia is $1\times10^4$ to $10^9$/g, preferably $1\times10^6$ to $10^9$/g.

Plants to be controlled by a herbicide of the present invention are non-useful plants having a hydrophobic surface, against which phytopathogenic microorganisms according to the present invention have pathogenicity. The plants referred to in the present invention are those which can grow in aqueous environments such as paddies, reservoirs, rivers, lakes, marshes and swamps. Hydrophytes and hygrophytes are also included. In particular, the plants referred to in the present invention are weeds grown in paddies. Examples of the weeds grown in paddies are those of the grass family (Poaceae), in particular barnyard grasses. Barnyard grasses are weeds belonging to genus Echinochloa, for example, *Echinochloa oryzicola, Echinochloa crus-galli* var. *formosensis, Echinochloa crus-galli* var. *crus-galli, Echinochloa crus-galli* var. *praticola, Echinochloa colona, Echinochloa pyramidalis, Echinochloa stagnina* and *Echinochloa haploclada.*

There are no particular restrictions on the growth period of the plants to be controlled. For example, a herbicide can be applied when the weeds in paddies are either covered with water or growing out of water. Even when the plants to be controlled are completely covered with water in the paddies, a high herbicidal activity can be attained dispersed and submersed phytopathogenic microorganisms adhere to and infect the plants by hydrophobic interaction.

A herbicide of the present invention can be sprayed on sites where plants to be controlled grow, for example on paddies, reservoirs, rivers, lakes, marshes and swamps, in particular on paddies. Accordingly a herbicide of the present invention is applied on the surface of the water in these sites.

There are no particular restrictions on the method of application as long as weeds are effectively controlled when applied, for example on paddies. The herbicide of the present invention can be applied, for example, by spraying, dropping or sprinkling.

EXAMPLES

The present invention will be explained by the following Examples and Comparative Examples. However, it is to be understood that the invention is not intended to be limited to these Examples.

Example 1

Cells of *Drechslera monoceras* MH-0015 were cultured on about 50 potato-dextrose agar medium plates for 14 days at 25° C., 20 ml of an aqueous 0.1% Triton X-100 solution were added and a suspension of conidia was recovered. The suspension was filtered using a Buchner funnel and the resulting conidia were washed with 2 L of water to remove the surfactant. The conidia thus obtained were thoroughly mixed at a concentration of $10^7$ conidia/g with a mixture, in which 0.3 g of Cellogen PR (Daiichi Kogyo Seiyaku Co., Ltd.), a pasting agent, was added to 3.7 g of TOALITE (Toa Kasei Co., Ltd.), a base, and the admixture was blended with 6.0 ml of water. The mixture was dried for 4 hours at 25° C. in air, the resulting material was lightly crushed and passed through a 250 $\mu$m screen and granules having a diameter of 250 $\mu$m or less were collected to produce a herbicide preparation.

Example 2

Conidia were treated in the same manner as described in Example 1 except that the dried and crushed material was passed through a 100 μm screen to obtain granules having a diameter of 100 μm or less for a herbicide preparation.

Example 3

Cells of *Drechslera ravanelii* MH-0042 were cultured on about 50 potato-dextrose agar medium plates for 14 days at 25° C., 20 ml of an aqueous 0.1% Triton X-100 solution were added, and a suspension of conidia was recovered. The suspension was filtered using a Buchner funnel and the resulting conidia were washed with 2 L of water to remove the surfactant. Next, the conidia thus obtained were thoroughly mixed at a concentration of $10^7$ conidia/g with a mixture, in which 0.3 g of Sanex P252 (Sanyo-Kokusaku Pulp Co., Ltd.), a pasting agent, was added to 3.7 g of zeolite, a base, and the admixture was blended with 6.0 ml of water. The mixture was dried for 4 hours at 25° C. in air, the resulting material was lightly crushed and passed through a 250 μm screen to obtain granules having a diameter of 250 mμmor less for a herbicide preparation.

Example 4

Conidia of *Drechslera monoceras* MH-0015 were recovered from the culture in the same manner as described in Example 1. The conidia were washed to completely remove the surfactant as described in Example 1 and then dried in air. The conidia thus obtained were throughly mixed at a concentration of $10^7$ conidia/g with 3.7 g of TOALITE (Toa Kasei Co., Ltd.) containing 10% by weight of a powdered surfactant EP-70G (Takemoto Oil & Fat Co., Ltd.) to obtain a powder preparation.

Example 5

Cells of *Drechslera monoceras* MH-2001 were cultured on about 50 potato-dextrose agar medium plates for 7 days at 25° C., 20 ml of an aqueous 0.1% Triton X-100 solution were added, and a suspension of conidia was recovered. The suspension was filtered using a Buchner funnel and the resulting conidia were washed with 2 L of water to remove the surfactant. Conidia thus obtained were thoroughly mixed at a concentration of $10^7$ conidia/g with TOALITE (Toa Kasei Co., Ltd.) to obtain a powder preparation.

Example 6

Cells of *Drechslera poae* MH-0122 were cultured in the same manner as described in Example 3 and a herbicide containing the resulting conidia was produced.

Comparative Example 1

Conidia of *Drechslera monoceras* MH-0015 were thoroughly mixed at a concentration of $10^7$ conidia/g with a mixture, in which 0.3 g of Cellogen PR, a pasting agent, was added to 3.7 g of TOALITE, a base, supplemented with 10% Newkalgen NV-410 (Takemoto Oil & Fat Co., Ltd.), a surfactant, and the admixture was blended with 6.0 ml of water. The conidia used were obtained in the same manner as described in Example 1 except that the surfactant was not removed. The resulting material was dried for 4 hours at 25° C. in air, lightly crushed and passed through a 250 μm screen, and granules having a diameter of 250 μm or less were collected to produce a herbicide containing the surfactant.

Comparative Example 2

The conidia were treated in the same manner as described in Comparative Example 1 except that the material was passed through a 100 μm screen to obtain granules having a diameter of 100 μm or less to produce a herbicide containing the surfactant.

Comparative Example 3

The conidia were prepared in the same manner as described in Example 1 except that after recovering from the agar medium, filtering, washing and removing the surfactant, the conidia were placed on a filter paper to completely remove water.

Comparative Example 4

The conidia were recovered from the cell culture of *Drechslera monoceras* MH-2001 in the same manner as described in Example 5 except that the surfactant was not removed. The conidia thus obtained were thoroughly mixed at a concentration of $5 \times 10^7$ conidia/g with TOALITE supplemented with 10% Newkalgen NV-410 (Takemoto Oil & Fat Co., Ltd.), surfactant, to prepare a wettable powder. Water was added to the wettable powder to make a suspension of $1 \times 10^5$ conidia/g, a wettable powder.

Test Example 1

Herbicidal activity was tested using the formulation prepared in Example 1. Plants of *Echinochloa oryzicola* were grown in glass beakers, which had a diameter of 8 cm and were filled with glass beads to a height of about 1.2 cm, under a 16-hour sunshine condition at 25° C. to the 1.5-leaf stage. The herbicide produced in Example 1 was sprinkled onto the beakers with the plants (equivalent to 300 g/a) and the beakers were filled with water to a depth of 5 cm. The experiment was triplicated using 20 plants each. One week later, all the plants were pulled out to determine whether their growing points were withered or not. Plants with the withered growing point were judged to be withered and those with no withered growing point were judged to have survived. Ratios of withering were calculated from the number of withered plants and the total number of plants. An average ratio of withering was obtained from results of the repeated experiments. The average ratio of withering obtained from the triplicated experiment was 87%.

Test Example 2

A herbicidal activity was tested using the herbicide prepared in Example 2 in the same manner as described in Test Example 1. The resulting average ratio of withering was 92%.

Test Example 3

A herbicidal activity was tested using the herbicide prepared in Example 3 in the same manner as described in Test Example 1. The resulting average ratio of withering was 90%.

Test Example 4

A herbicidal activity was tested using the herbicide prepared in Example 4 in the same manner as described in Test Example 1. The resulting average ratio of withering was 95%.

Test Example 5

The herbicidal activity was carried out using the herbicide prepared in Comparative Example 1 in the same manner as described in Test Example 1. The same number of conidia as in Test Example 1, i.e., equivalent to 300 g/a, was used. The resulting average ratio of withering was 48%.

Test Example 6

The herbicidal activity was tested using the herbicide prepared in Comparative Example 2 in the same manner as described in Test Example 1. The same number of conidia as in Test Example 1, i.e., equivalent to 300 g/a, was used. The resulting average ratio of withering was 54%.

Test Example 7

The herbicidal activity was tested using the herbicide prepared in Comparative Example 3 in the same manner and with the same number of conidia as in Test Example 1. Most of the conidia float on the surface of water and the resulting average ratio of withering was 5%.

Test Example 8

Adhesiveness of conidia

Relationship between adhesiveness of conidia and herbicidal activity was evaluated as follows:

Plants of *Echinochloa oryzicola* were grown in glass beakers, which had a diameter of 8 cm and were filled with glass beads to a height of about 1.2 cm, under a 16-hour sunshine condition at 25° C. to the 1.5-leaf stage. The plants were thinned out to adjust the growth stage and about 20 plants were ultimately left in each beaker. The beakers with the plants were filled with water to a depth of 5 cm and sprinkled with the powder prepared in Example 5 or the wetting powders prepared in Comparative Example 4 at concentrations equivalent of $3 \times 10^9$, $10 \times 10^9$ and $30 \times 10^9$ conidia/a. The experiment was triplicated using 20 plants each.

Two days after sprinkling, 10 leaves were taken and washed to remove conidia which had not adhered. The leaves were sandwiched between slide glasses and observed under a microscope. The number of conidia attach to the front and back of leaves for a length of 1 cm was counted.

A week after sprinkling, all the plants were pulled out and spread on a filter paper to determine whether the growing point was withered or not and to calculate ratios of withering. Results are shown in Table 1.

TABLE 1

| Number of sprinkled conidia (per are) | Ratio of withering (%) | | Number of adhered conidia (per cm) | |
|---|---|---|---|---|
| | Powder | Wetting powder | Powder | Wetting powder |
| $3 \times 10^9$ | 83 | 47 | 16 | 5 |
| $10 \times 10^9$ | 100 | 53 | 40 | 6 |
| $30 \times 10^9$ | 100 | 60 | 53 | 12 |

What is claimed is:

1. A herbicide containing phytopathogenic microorganisms for surface application on water comprising phytopathogenic microorganisms which are pathogenic against non-useful plants having a hydrophobic surface, and are themselves hydrophobic on the surface but with virtually no adhered surfactant, and a submersible base.

2. The herbicide containing phytopathogenic microorganisms for surface application on water according to claim 1 wherein the herbicide is a solid formulation.

3. The herbicide containing phytopathogenic microorganisms for surface application on water according to claim 2 wherein the solid herbicide is a powder, granule or powdery granule formulation.

4. The herbicide containing phytopathogenic microorganisms for surface application on water according to claim 2 wherein the phytopathogenic microorganisms are those belonging to genus Drechslera.

5. The herbicide containing phytopathogenic microorganisms for surface application on water according to claim 4 wherein the phytopathogenic microorganisms belonging to genus Drechslera are those belonging to *Drechslera monoceras, Drechslera ravenelii* or *Drechslera poae*.

6. The herbicide containing phytopathogenic microorganisms for surface application on water according to claim 1 wherein the phytopathogenic microorganisms are those belonging to genus Drechslera.

7. The herbicide containing phytopathogenic microorganisms for surface application on water according to claim 6 wherein the phytopathogenic microorganisms belonging to genus Drechslera are those belonging to *Drechslera monoceras, Drechslera ravenelii* or *Drechslera poae*.

8. A method of producing a herbicide containing phytopathogenic microorganisms for surface application on water, wherein phytopathogenic microorganisms which are pathogenic against non-useful plants having a hydrophobic surface, and are themselves hydrophobic on the surface, are produced, and said phytopathogenic microorganisms are adhered to or combined with a submersible base, while retaining the surface hydrophobicity of the phytopathogenic microorganisms.

9. The method of producing a herbicide according to claim 8 wherein the herbicide is a solid formulation.

10. The method of producing a herbicide according to claim 9 wherein the solid formulation is a powder, granule or powdery granule formulation.

11. The method of producing a herbicide according to claim 9 wherein the phytopathogenic microorganisms are those belonging to genus Drechslera.

12. The method of producing a herbicide according to claim 11 wherein the phytopathogenic microorganisms belonging to genus Drechslera are those belonging to *Drechslera monoceras, Drechslera ravenelii* or *Drechslera poae*.

13. The method of producing a herbicide according to claim 8 wherein the phytopathogenic microorganisms are those belonging to genus Drechslera.

14. The method of producing a herbicide according to claim 13 wherein the phytopathogenic microorganisms belonging to genus Drechslera are those belonging to *Drechslera monoceras, Drechslera ravenelii* or *Drechslera poae*.

15. A method of producing a herbicide containing phytopathogenic microorganisms for surface application on water, wherein phytopathogenic microorganisms, which are pathogenic against non-useful plants having a hydrophobic surface, and are themselves hydrophobic on the surface, are produced, and said phytopathogenic microorganisms are dispersed among particles of a submersible base, while retaining the surface hydrophobicity of the phytopathogenic microorganisms.

16. The method of producing a herbicide according to claim 15 wherein the herbicide is a solid formulation.

17. The method of producing a herbicide according to claim 16 wherein the solid formulation is a powder, granule or powdery granule formulation.

18. The method of producing a herbicide according to claim 16 wherein the phytopathogenic microorganisms are those belonging to genus Drechslera.

19. The method of producing a herbicide according to claim 18 wherein the phytopathogenic microorganisms belonging to genus Drechslera are those belonging to *Drechslera monoceras, Drechslera ravenelii* or *Drechslera poae*.

20. The method of producing a herbicide according to claim 15 wherein the phytopathogenic microorganisms are those belonging to genus Drechslera.

21. The method of producing a herbicide according to claim 20 wherein the phytopathogenic microorganisms belonging to genus Drechslera are those belonging to *Drechslera monoceras, Drechslera ravenelii* or *Drechslera poae*.

* * * * *

UNITED STATES PATENT AND TRADEMARK OFFICE
CERTIFICATE OF CORRECTION

PATENT NO. : 6,066,595
DATED : May 23, 2000
INVENTOR(S) : Kazuto ISHIHARA et al.

It is certified that error appears in the above-identified patent and that said Letters Patent is hereby corrected as shown below:

Title page,
Section [30], change priority document number to --8-292461--.

Signed and Sealed this

Fifteenth Day of May, 2001

Attest:

NICHOLAS P. GODICI

Attesting Officer    Acting Director of the United States Patent and Trademark Office